US00PP35954P2

(12) United States Plant Patent
Jachertz

(10) Patent No.: US PP35,954 P2
(45) Date of Patent: Jul. 2, 2024

(54) ***GASTERALOE* PLANT NAMED 'BINL-19037'**

(50) Latin Name: ***Gasteraloe* hybrid**
Varietal Denomination: BINL-19037

(71) Applicant: Botanical Innovation, BV, Wageningen (NL)

(72) Inventor: Christian Jachertz, Amposta (ES)

(73) Assignee: Botanical Innovation B.V. (NL)

( * ) Notice: Subject to any disclaimer, the term of this patent is extended or adjusted under 35 U.S.C. 154(b) by 0 days.

(21) Appl. No.: 18/387,396

(22) Filed: Nov. 6, 2023

(51) Int. Cl.
*A01H 5/12* (2018.01)
*A01H 6/00* (2018.01)

(52) U.S. Cl.
USPC ..... Plt./373
CPC ..... *A01H 6/00* (2018.05)

(58) Field of Classification Search
USPC ..... Plt./373
CPC ..... A01H 5/12
See application file for complete search history.

*Primary Examiner* — Kent L Bell
(74) *Attorney, Agent, or Firm* — Cassandra Bright

(57) ABSTRACT

A new and distinct cultivar of *Gasteraloe* plant named 'BINL-19037' is disclosed, characterized by open, flat-growing rosettes with unique coloring of green leaves with scattered white lenticel dots. The new variety is a *Gasteraloe*, typically used as an ornamental plant.

2 Drawing Sheets

Figure 1:
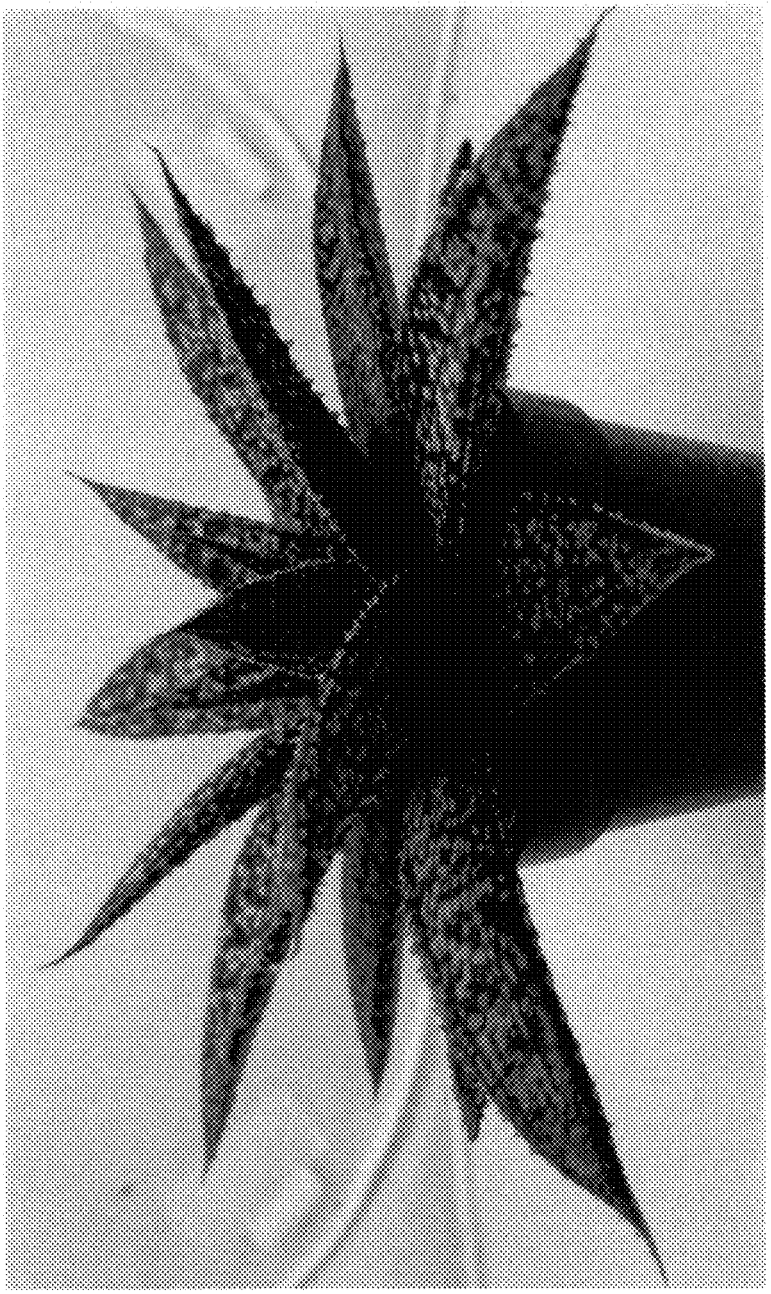

Latin name of the genus and species: *Gasteraloe* hybrid.
Variety denomination: 'BINL-19037'.

BACKGROUND OF THE INVENTION

The new cultivar is a product of a planned breeding program to produce distinct and improved performing *Gasteraloe* varieties. The new variety was selected as a seedling resulting from the crossing made by the inventor, Christian Jachertz , a citizen of Spain, in 2017. The seed parent is the unpatented *Gasteria carinata* var. *verrucosa* '#1041', a variety from the inventor's breeding line. The pollen parent is the unpatented *Aloe aristata* '#2041', also from the inventor's breeding line. The new variety was selected by the inventor in 2018 as a single plant within the progeny of the stated cross at a commercial greenhouse in Amposta, Spain.

Asexual reproduction of the new cultivar 'BINL-19037' by terminal cuttings was first performed in Amposta, Spain at a commercial greenhouse in March 2019, and has shown that the unique features of this cultivar are stable and reproduced true to type through successive generations of asexual reproduction.

SUMMARY OF THE INVENTION

The cultivar 'BINL-19037' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BINL-19037'. These characteristics in combination distinguish 'BINL-19037' as a new and distinct *Gasteraloe* cultivar:

1. Unique color combination of scattered white lenticel dots on green leaves.
2. Open and flat-growing rosette-shaped plant.

PARENT COMPARISONS

Plants of the new cultivar 'BINL-19037' are similar to plants of the female parent in most horticultural characteristics, however, plants of the new cultivar 'BINL-19037' differ in the following characteristics:

1. Plants of the new variety have a rosette shape, while plants of the seed parent have in line growing leaves.
2. Leaves of the new variety are shorter than leaves of the seed parent.
3. Plants of the new variety are faster growing than plants of the seed parent.

Plants of the new cultivar 'BINL-19037' are similar to plants of the male parent in most horticultural characteristics, however, plants of the new cultivar 'BINL-19037' differ in the following characteristics:

1. Leaves of the new variety are darker green with more white lenticel dots than leaves of the pollen parent.
2. Plants of the new variety have an open rosette shape, while plants of the pollen parent have a full rosette shape with many more densely growing leaves.
3. Lenticel dots of the new variety are larger than lenticel dots of the pollen parent.

COMMERCIAL COMPARISONS

Plants of the new cultivar 'BINL-19037' are similar to plants of the commercial variety *Gasteraloe* 'D Delta', U.S. Plant Pat. No. 30,905. However, plants of the new cultivar differ in the following characteristics:

1. Leaf color of the new variety is lighter green than the leaf color of this comparator.
2. Leaves of the new variety have many more white lenticel dots than leaves of this comparator.

Plants of the new cultivar 'BINL-19037' are similar to plants of the commercial variety *Gasteraloe* 'Flow', U.S.

Plant Pat. No. 25,667. However, plants of the new cultivar differ in the following characteristics:

1. Leaf color of the new variety is lighter green than the leaf color of this comparator.
2. Leaves of the new variety have many more white lenticel dots than leaves of this comparator.

BRIEF DESCRIPTION OF THE PHOTOGRAPHS

The accompanying photograph in FIG. 1 illustrates in full color a typical plant of 'BINL-19037' grown in a greenhouse. The plant is approximately 40 weeks of age.

Figure 2:
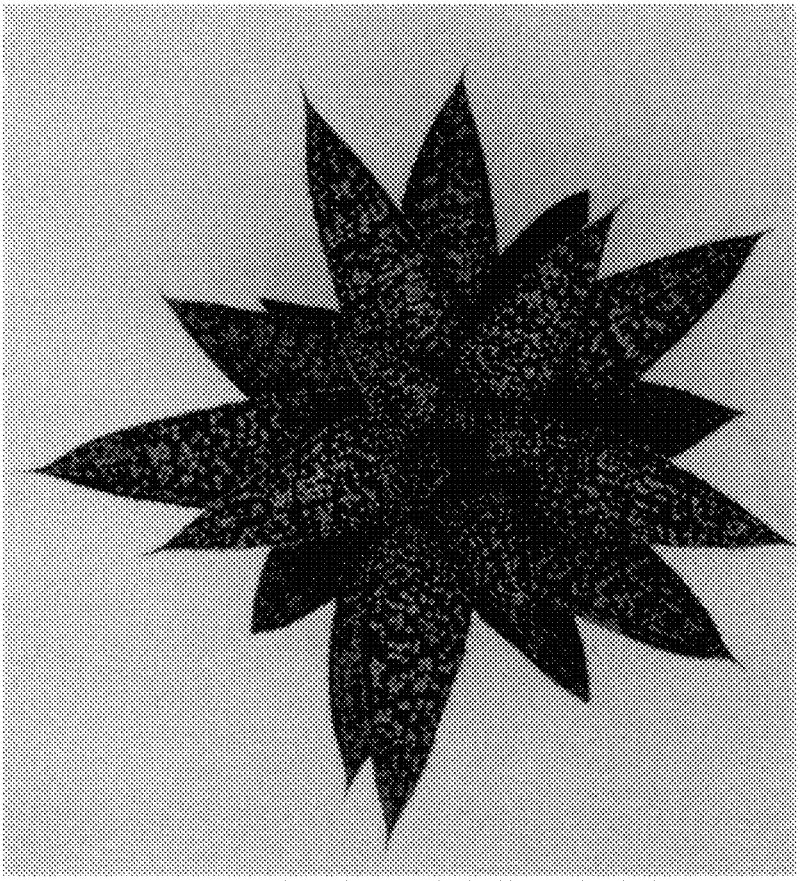

FIG. 2 illustrates a top-view of the same plant.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'BINL-19037' plants at 40 weeks of age, grown in a greenhouse in Amposta, Spain during August. The growing temperature ranged from 15° C. to 18° C. at night to 18° C. to 20° C. during the day. Measurements and numerical values represent averages of typical plants.

Botanical classification: *Gasteraloe* hybrid 'BINL-19037'.

PROPAGATION

Time to initiate roots: About 14 days at approximately 20° C. in summer or winter.

Time to produce rooted cutting: About 80 days at 20° C. in summer; 90 days at 20° C. in winter.

Description of roots: Fibrous, thick, moderately dense, freely branching. Brown in color, not accurately measured with RHS chart.

PLANT

Plant type: Perennial potted plant.
Plant shape: Broad obovate to orbicular.
Growth habit: Basal rosette of leaves.
Plant spread: Average 11.2 cm.
Height: Average 9 cm.
Growth rate: Low to moderate.
Plant vigor: Low to moderate.
Age of plant described: Approximately 40 weeks.
Branching habit: Leaves in basal rosettes.
Pinching: Pinching not required.
Number of primary (main) branches per plant: Average 1 basal rosette.
Number of secondary (lateral) branches per plant: None.

FOLIAGE

Leaf:

*Arrangement.*—Single rosette.
*Quantity.*—Average 22 per rosette.
*Average length.*—6.9 cm.
*Average width.*—1.8 cm.
*Shape.*—Lanceolate, succulent.
*Aspect.*—Flat to very slightly concave.
*Apex.*—Narrow acute with a soft mucronate tip.
*Base.*—Broad cuneate.
*Margin.*—Finely pustulate-dentate, average length of teeth: 0.5 mm, average width of teeth: 0.4 mm, colored RHS Greyed-Green 194B.
*Texture.*—Top surface: Densely pustulate, placed on lamina in irregular axial lines, average diameter: 0.1 cm, average height: less than 0.2 mm, colored RHS Greyed-Green 189D, with a small White 155D central dot. Lower surface: Densely pustulate, placed on lamina in irregular axial lines, average diameter: 0.1 cm, average height: less than 0.2 mm, colored RHS Greyed-Green 191C, with a small Greyed-Green 191D central dot.
*Pubescence.*—None.
*Luster, upper side.*—Moderately glossy.
*Luster, under side.*—Moderately glossy.
*Rugosity, upper side.*—Non-rugose.
*Rugosity, under side.*—Non-rugose.
*Color.*—Young foliage upper side: RHS Green 139A, fading to Yellow-Green 152D towards the base. Young foliage under side: RHS Green 139A, fading to Yellow-Green 152C and 152D towards the base. Mature foliage upper side: A blend of RHS Yellow-Green 147A and Greyed-Green N189A, fading to Yellow-Green 146C towards the base; base Greyed-White 156C. Mature foliage under side: A blend of RHS Green 139A and Greyed-Green N189A, fading to Green 143A towards the base; base Greyed-White 156A.
*Venation.*—Pattern: Parallel. Venation color upper side: A blend of RHS Yellow-Green 147A and Greyed-Green N189A, fading to Yellow-Green 146C towards the base; base Greyed-White 156C. Venation color under side: A blend of RHS Green 139A to Greyed-Green N189A, fading to Green 143A towards the base; base Greyed-White 156A.

OTHER CHARACTERISTICS

Flowers: None observed to date.
Seeds and fruits: None observed to date.
Disease/pest resistance: Plants of the new *Gasteraloe* have not been noted to be resistant or susceptible to pathogens and pests common to *Gasteraloe*.
Temperature tolerance: Tolerates temperatures up to 40° C. Hardy to USDA zones 10 to 12. Low tolerance to rain. High tolerance to wind.

What is claimed is:

1. A new and distinct cultivar of *Gasteraloe* plant named 'BINL-19037' as herein illustrated and described.

* * * * *